US00PP11204P

United States Patent [19]

VandenBerg

[11] Patent Number: Plant 11,204

[45] Date of Patent: Feb. 1, 2000

[54] CHRYSANTHEMUM PLANT NAMED 'YOLIMA'

[75] Inventor: Cornelis P. VandenBerg, Salinas, Calif.

[73] Assignee: Yoder Brothers, Inc., Barberton, Ohio

[21] Appl. No.: 09/112,201

[22] Filed: Jul. 9, 1998

[51] Int. Cl.[7] ..... A01H 5/00

[52] U.S. Cl. ..... Plt./286

[58] Field of Search ..... Plt./286, 297

*Primary Examiner*—Howard J. Locker

*Attorney, Agent, or Firm*—C. A. Whealy

[57] ABSTRACT

A distinct cultivar of Chrysanthemum plant named 'Yolima', characterized by its compact and uniformly mounded plant habit; freely branching habit; uniform and early flowering; anemone spray-type inflorescences that are about 5.5 cm in diameter; attractive pink-colored ray florets and light green to dark pink-tipped disc florets; numerous inflorescences per plant; and excellent postproduction longevity with inflorescences and leaves maintaining good substance and color for about four or five weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yolima. The plant is being marketed under the name Lima.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in January, 1992, in Salinas, Calif., of a proprietary Chrysanthemum seedling selection code number YB-4473 as the male, or pollen, parent with the commercial Chrysanthemum cultivar Dinara (not patented) as the female, or seed, parent.

The new Chrysanthemum was discovered and selected by the inventor as a flowering plant within the progeny of the stated cross in a controlled environment in Salinas, Calif., in January, 1993. The selection of this plant was based on its desirable inflorescence form and floret colors and excellent post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yolima has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yolima'. These characteristics in combination distinguish 'Yolima' as a new and distinct Chrysanthemum:

1. Compact and uniformly mounded plant habit.
2. Freely branching habit, dense plants.
3. Uniform and early flowering.

4. Anemone spray-type inflorescences that are about 5.5 cm in diameter.
5. Attractive pink-colored ray florets and light green to dark pink-tipped disc florets.
6. Numerous inflorescences per plant.
7. Excellent postproduction longevity with inflorescences and leaves maintaining good substance and color for about four or five weeks in an interior environment.

The new Chrysanthemum can be compared to the Chrysanthemum cultivar Pink Papillon (disclosed in U.S. Plant Pat. No. 9,825). However in side-by-side comparisons in Salinas, Calif., and Leamington, Ontario, Canada, under commercial practice, plants of the new Chrysanthemum differed from plants of the cultivar Pink Papillon in the following characteristics:

1. Plants of the new Chrysanthemum have larger and more deeply lobed leaves than plants of the cultivar Pink Papillon.
2. Plants of the new Chrysanthemum have anemone-type inflorescences whereas plants of the cultivar Pink Papillon have single-type inflorescences.
3. Plants of the new Chrysanthemum have longer and more narrow ray florets than plants of the cultivar Pink Papillon.
4. Plants of the new Chrysanthemum have larger inflorescences than plants of the cultivar Pink Papillon.
5. Disc florets of plants of the new Chrysanthemum have significantly less pollen than plants of the cultivar Pink Papillon.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yolima'.

The photograph at the bottom of the first sheet is a close-up view of a typical inflorescences of plants of 'Yolima'.

The photograph at the top of the second sheet is a close-up view of upper (left) and lower (right) surfaces of typical leaves and inflorescences of plants of 'Yolima'.

The photograph at the bottom of the second sheet comprises a side perspective view of typical plants of 'Yolima' (left) and 'Pink Papillon ' (right) showing the differences in plant shape, inflorescence type, and inflorescence size. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yolima.

Commercial classification: Anemone spray-type pot Chrysanthemum.

Parentage:

*Male or pollen parent.*—Proprietary *Dendranthema grandiflora* seedling selection, code number YB-4473.

*Female or seed parent.*—*Dendranthema grandiflora* cultivar Dinara.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous anemone spray-type pot Chrysanthemum. Inverted triangle. Stems initially upright, then somewhat spreading giving a uniformly mounded appearance to the plant. Freely branching; about four or five lateral branches develop after removal of terminal apex (pinching), dense and full plants.

*Plant height.*—Compact, about 18 cm.

*Plant width.*—About 35 cm.

*Foliage description.*—Arrangement: Alternate. Length: About 6.3 cm. Width: About 4.8 cm. Apex: Mucronate. Base: Attenuate. Margin: Palmately lobed, sinuses between lateral lobes parallel to overlapping. Texture: Upper and lower surfaces slightly pubescent. Veins prominent on lower surface. Petiole length: About 2.5 cm. Color: Young foliage upper surface: 147A. Young foliage lower surface: Slightly darker than 147B. Mature foliage upper surface: 147A, shiny. Mature foliage lower surface: Slightly darker than 147B. Venation upper surface: 147A to 147B. Venation lower surface: 147B.

Inflorescence description:

*Appearance.*—Anemone spray-type inflorescence form with oblong shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to about two weeks of long day/short night conditions after planting followed by photoinductive short day/long night conditions flower about eight weeks later.

*Postproduction longevity.*—Inflorescences and leaves will maintain good color and substance for about four or five weeks in an interior environment.

*Quantity of Inflorescences.*—About seven inflorescences per terminal with about 32 inflorescences per plant.

*Inflorescence bud.*—Height: About 6.3 mm. Diameter: About 8.1 mm. Color: Close to 137A.

*Inflorescence size.*—Diameter: About 5.5 cm. Depth (height): About 1.4 cm. Diameter of disc: About 2.1 cm.

*Ray florets.*—Shape: Oblong with very short corolla tube. Aspect: Straight, concave. Length: About 2.6 cm. Width: About 8 mm. Apex: Acute or emarginate. Margin: Entire. Texture: Smooth, glabrous. Number of ray florets per inflorescence: About 26. Color: When opening, upper surface: Close to 70C. When opening, lower surface: 70B to 70C. Fully opened, upper surface: Background of 62B to 62C to 62D with streaks of 70A to 70B. Fully opened, lower surface: Mostly 70A to 70B, lighter towards margin.

*Disc florets.*—Shape: Enlarged tubular. Apex: Dentate, flared. Length: About 1 cm. Width: Apex: About 3 mm. Base: About 1 mm. Number of disc florets per inflorescence: About 127. Color: Immature: 143A to 154A. Mature: Apex: 70A/70B. Mid-section and base: 144B.

*Peduncle.*—Aspect: Flexible, strong, angled about 35° to stem. Length: First peduncle: About 1.2 cm. Fourth peduncle: About 2.8 cm. Texture: Pubescent. Color: 137A.

*Reproductive organs.*—Androecium: Present on disc florets only. Anther color: 7A. Pollen: Amount: Moderate to low. Color: 9A. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Yolima', as illustrated and described.

* * * * *

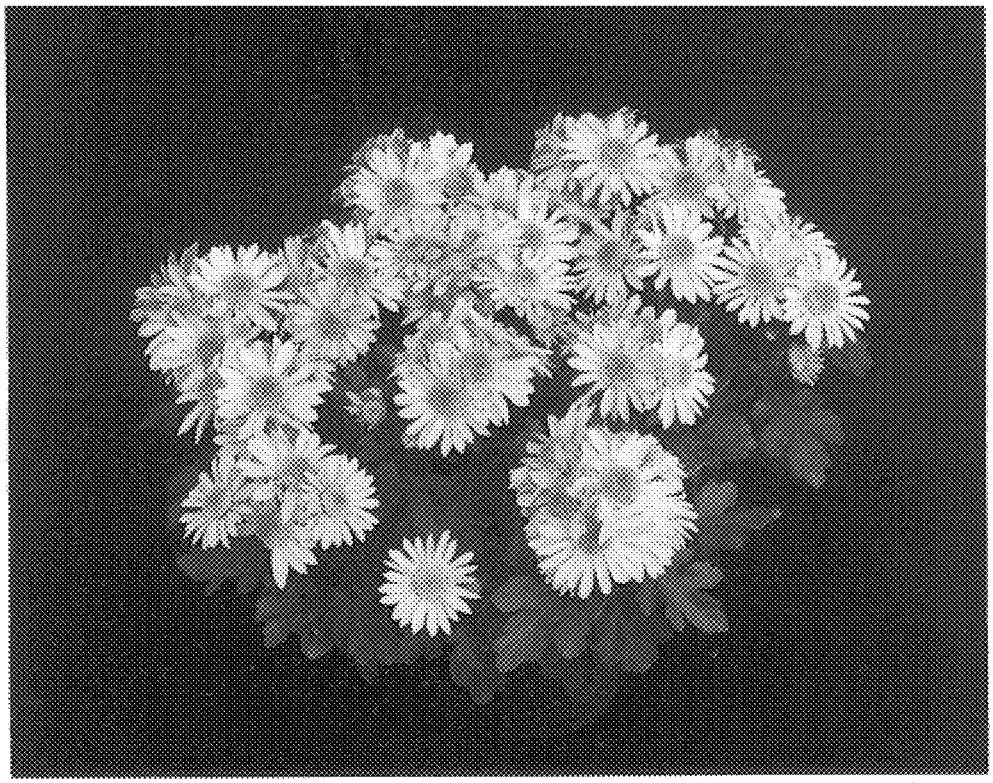
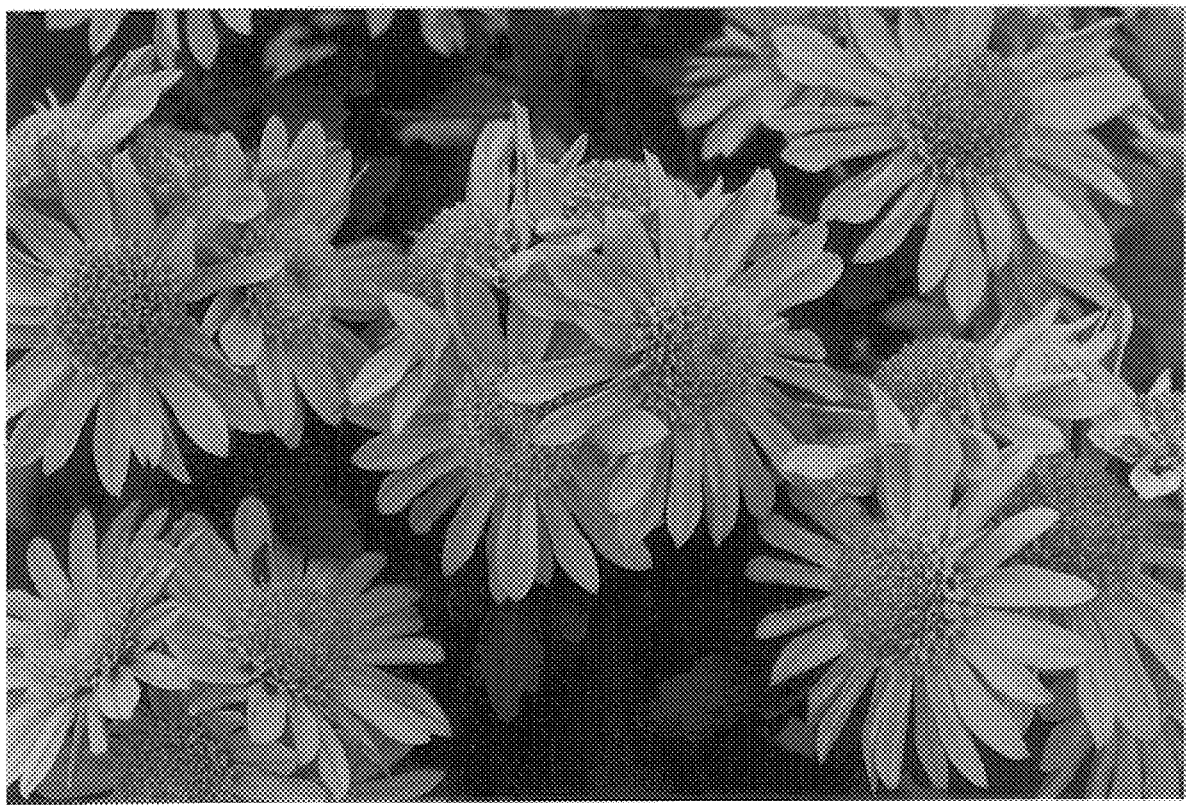

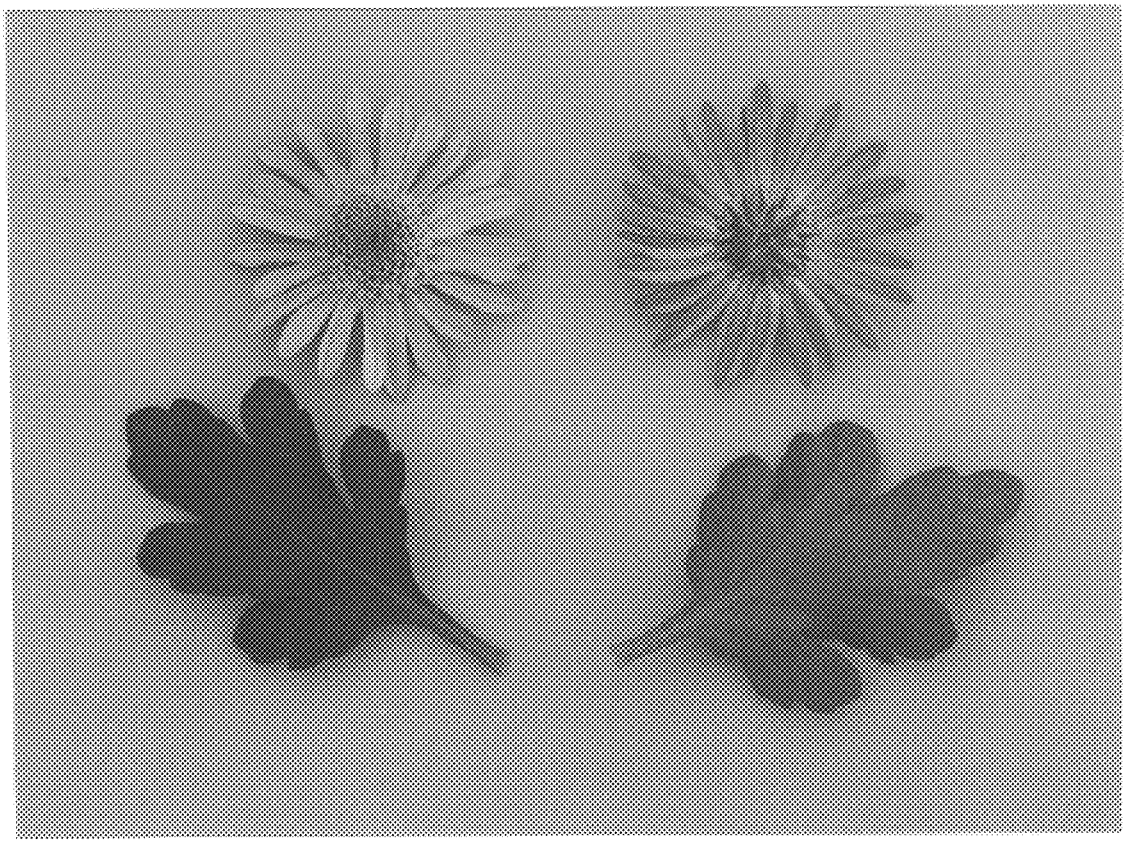
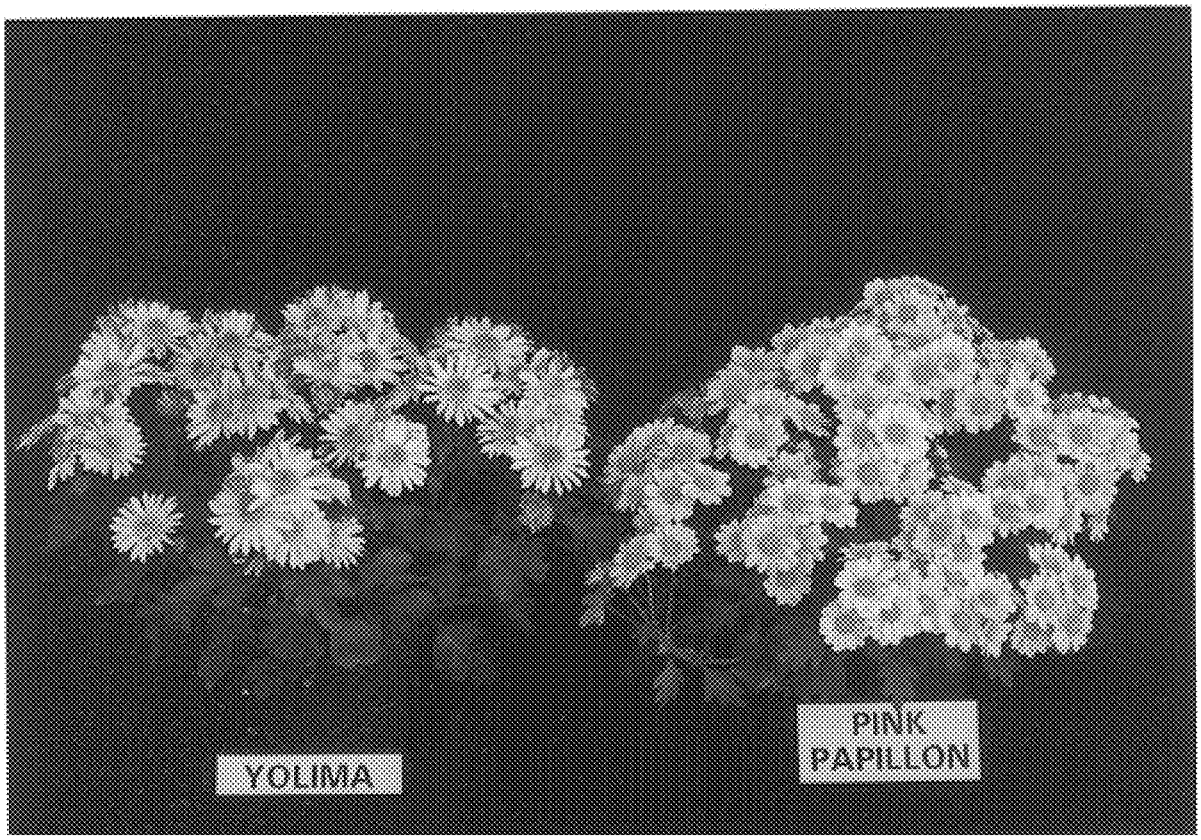
YOLIMA
PINK
PAPILLON